US011357390B2

(12) United States Patent
Wieters et al.

(10) Patent No.: US 11,357,390 B2
(45) Date of Patent: Jun. 14, 2022

(54) OPTICAL SYSTEM FOR A STEREO VIDEO ENDOSCOPE

(71) Applicant: OLYMPUS WINTER & IBE GMBH, Hamburg (DE)

(72) Inventors: Martin Wieters, Barsbuettel (DE); Peter Schouwink, Ahrensburg (DE); Jianxin Zhao, Hamburg (DE); Alrun Thuemen, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 242 days.

(21) Appl. No.: 16/844,370

(22) Filed: Apr. 9, 2020

(65) Prior Publication Data
US 2020/0229685 A1 Jul. 23, 2020

Related U.S. Application Data

(63) Continuation of application No. PCT/EP2018/077037, filed on Oct. 4, 2018.

(30) Foreign Application Priority Data

Oct. 13, 2017 (DE) ..................... 10 2017 123 896.4

(51) Int. Cl.
*A61B 1/00* (2006.01)
*G02B 23/24* (2006.01)
*A61B 1/05* (2006.01)

(52) U.S. Cl.
CPC ...... *A61B 1/00193* (2013.01); *A61B 1/00096* (2013.01); *A61B 1/00179* (2013.01);
(Continued)

(58) Field of Classification Search
CPC ............ A61B 1/00179; A61B 1/00096; A61B 1/00193; A61B 1/05; G02B 23/243; G02B 23/2415; G02B 23/2484
See application file for complete search history.

(56) References Cited

U.S. PATENT DOCUMENTS 4,745,470 A 5/1988 Yabe et al.
6,361,491 B1 3/2002 Hasegawa et al.
(Continued)

FOREIGN PATENT DOCUMENTS

CN 103070660 A 5/2013
DE 10 2011 005 255 A1 9/2012
(Continued)

OTHER PUBLICATIONS

International Search Report dated Dec. 3, 2018 received in PCT/EP2018/077037.
(Continued)

*Primary Examiner* — Alexandra L Newton
*Assistant Examiner* — Shankar Raj Ghimire
(74) *Attorney, Agent, or Firm* — Scully, Scott, Murphy & Presser, P.C.

(57) ABSTRACT

An optical system for a stereo video endoscope including: first and second lens system channels each having optical elements in identical configurations, the optical elements being arranged in a same position along first and second optical axes, respectively, an optical axis of first and second optical elements coincide with the first and second optical axes, respectively, first and second cross-sectional areas of the first and second optical elements are inscribed in first and second circumferential circles, respectively, centers of first and second circumferential circles each coincide with the first and second optical axes, respectively, to define a maximum radius of the first optical element and the second optical element, the first and second circumferential circles overlap one another, and circumferential shapes of the first and second optical elements deviate from the first and second circumferential circles circumscribing them such that the first and second optical elements do not contact.

10 Claims, 8 Drawing Sheets

(52) U.S. Cl.
CPC .............. *A61B 1/05* (2013.01); *G02B 23/243* (2013.01); *G02B 23/2415* (2013.01); *G02B 23/2484* (2013.01)

(56) References Cited

U.S. PATENT DOCUMENTS

| | | | |
|---|---|---|---|
| 10,088,665 B2 * | 10/2018 | Zhao | G02B 23/243 |
| 2002/0161278 A1 * | 10/2002 | Nakamura | G02B 23/243 600/111 |
| 2003/0125608 A1 * | 7/2003 | Igarashi | A61B 1/00101 600/166 |
| 2005/0001899 A1 | 1/2005 | Banju et al. | |
| 2005/0131280 A1 | 6/2005 | Rovegno | |
| 2009/0040606 A1 | 2/2009 | Lee | |
| 2009/0160935 A1 * | 6/2009 | Rovegno | A61B 1/00193 348/E7.085 |
| 2009/0168166 A1 | 7/2009 | Obrebski | |
| 2009/0296235 A1 | 12/2009 | Igarashi | |
| 2012/0147147 A1 | 6/2012 | Park et al. | |
| 2012/0249988 A1 | 10/2012 | Runde et al. | |
| 2013/0041216 A1 | 2/2013 | McDowall | |
| 2013/0057748 A1 | 3/2013 | Duparre et al. | |
| 2014/0177043 A1 * | 6/2014 | Togino | G02B 13/04 359/367 |
| 2014/0357951 A1 * | 12/2014 | Muller | H04N 13/218 600/111 |
| 2015/0168710 A1 | 6/2015 | Zobel | |
| 2016/0154231 A1 * | 6/2016 | Zhao | G02B 23/2453 348/45 |
| 2016/0192824 A1 * | 7/2016 | Ichihashi | A61B 1/00101 348/65 |
| 2017/0363856 A1 | 12/2017 | Schoeler | |
| 2017/0371144 A1 * | 12/2017 | Ichihashi | A61B 1/00193 |
| 2018/0180868 A1 * | 6/2018 | Zhao | G02B 23/243 |
| 2018/0242823 A1 * | 8/2018 | Ichihashi | G02B 23/2461 |
| 2018/0295265 A1 * | 10/2018 | Suga | H04N 5/2254 |
| 2020/0390317 A1 * | 12/2020 | Thuemen | A61B 1/00121 |

FOREIGN PATENT DOCUMENTS

| | | |
|---|---|---|
| DE | 10 2013 215 422 A1 | 2/2015 |
| DE | 10 2015 203 357 A1 | 8/2016 |
| DE | 10 2015 217 079 A1 | 3/2017 |
| EP | 2 806 301 A1 | 11/2014 |
| EP | 3 037 864 A2 | 6/2016 |
| JP | H0856891 A | 3/1996 |
| JP | H09101465 A | 4/1997 |
| JP | H09-127435 A | 5/1997 |
| JP | H1156757 A | 3/1999 |
| JP | H11352416 A | 12/1999 |
| JP | 2000292713 A | 10/2000 |
| JP | 2001-145640 A | 5/2001 |
| JP | 2003325441 A | 11/2003 |
| JP | 2005312555 A | 11/2005 |
| JP | S6365840 B2 | 8/2018 |
| JP | S6366525 B2 | 8/2018 |
| WO | 2007/082691 A2 | 7/2007 |
| WO | 2012/119693 A1 | 9/2012 |
| WO | 2013108500 A1 | 7/2013 |
| WO | 2015/134060 A1 | 9/2015 |
| WO | 2017104276 A1 | 6/2017 |

OTHER PUBLICATIONS

Japanese Office Action dated Mar. 15, 2022 received in 2020-520451.

* cited by examiner

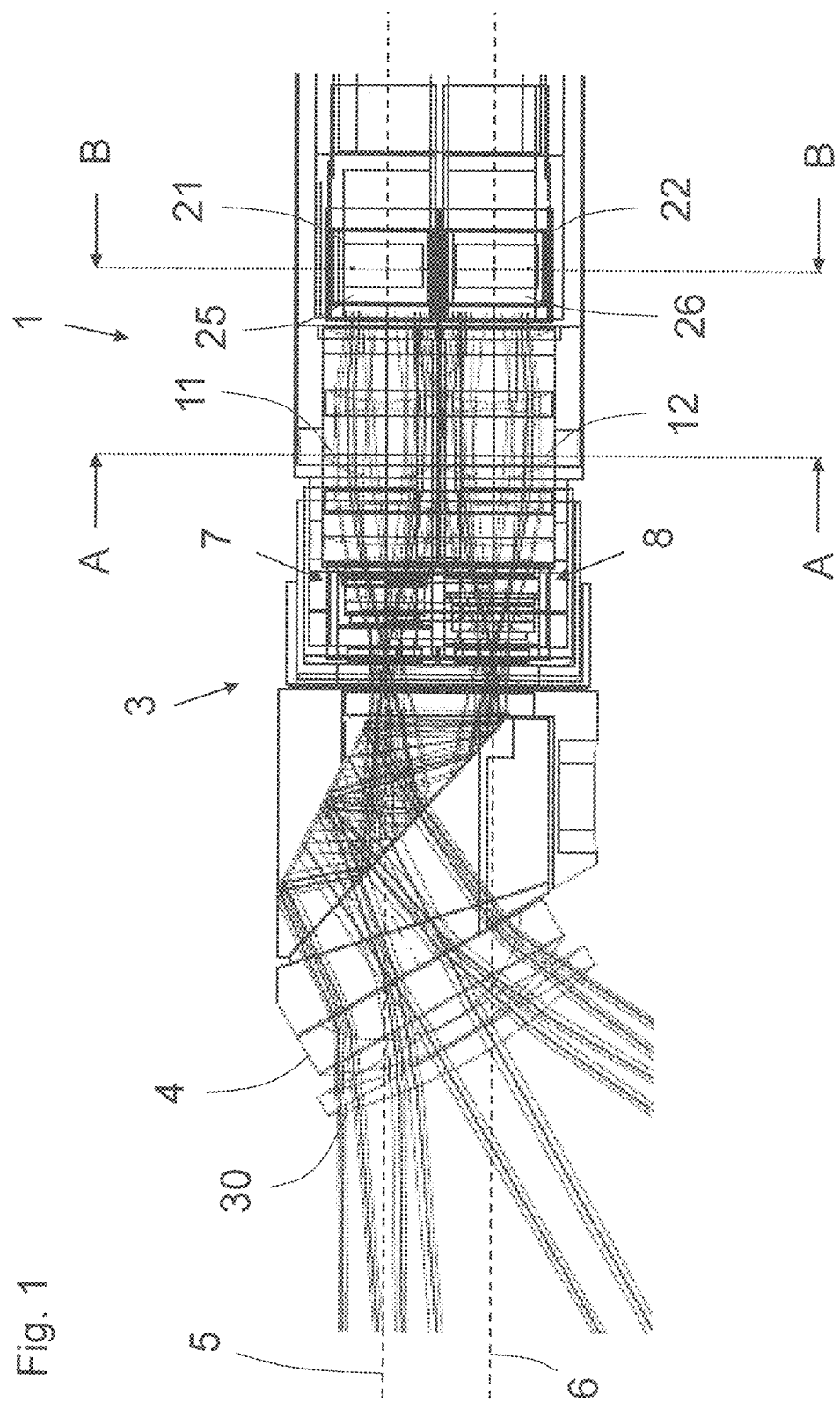

OPTICAL SYSTEM FOR A STEREO VIDEO ENDOSCOPE

CROSS-REFERENCE TO RELATED APPLICATION

The present application is a continuation of PCT/EP2018/077037 filed on Oct. 4, 2018, which is based upon and claims the benefit to DE 10 2017 123 896.4 filed on Oct. 13, 2017, the entire contents of each of which are incorporated herein by reference.

BACKGROUND

Field

The present disclosure relates to an optical system and more particularly to an optical system for a stereo video endoscope as well as to a stereo video endoscope.

Prior Art

Stereo video endoscopes are deployed in medicine to provide an attending physician with a spatial representation of the interior of a patient's body. To this end, light beams entering an optical system of the endoscope are guided in two parallel running and configured lens system channels, which depict the light beams on two separate image sensors. In this way, images of the observed region are captured at slightly different viewing angles. If these images are viewed such that each eye in each case perceives the image or the images of a lens system channel, for example with the aid of shutter glasses, a spatial impression of the observed region is created. This is referred to as stereoscopy. Such a stereo video endoscope is disclosed, for example, in DE 10 2013 215 422 A1.

The distance of the optical axes of the lens system channels is crucial for the strength of the spatial impression. If this distance is too small, only a weak spatial impression is created. Care must therefore be taken to ensure that the distance of the lens system channels is correct when constructing a stereo video endoscope.

At the same time, when constructing endoscopes, care must be taken to ensure that the outer diameter of the endoscopes is as small as possible in order to minimize the stress associated with an endoscopic examination for the patient. One difficulty arises from the fact that the optical elements arranged in the lens system channels, for example lenses, are to have as large a cross-sectional area as possible so that a high image quality is attained. If these optical elements are too large, they can no longer be arranged next to one another in the casing tube of the endoscope. Furthermore, additional care must be taken to ensure that the correct distance of the optical axes is also observed in the case of large optical elements. Therefore, a compromise between these requirements must be found with stereo video endoscopes.

SUMMARY

An object consists of providing an optical system for a stereo video endoscope as well as a stereo video endoscope, with which an improvement of the image quality, the stereoscopic effect and/or an enlargement of the field of view is/are achieved without enlarging the outer diameter of the endoscope shaft.

Such object can be achieved by an optical system for a stereo video endoscope, comprising a first lens system channel and a second lens system channel for a stereoscopic representation of a region lying outside of the stereo video endoscope, wherein the lens system channels are arranged in parallel to one another and each comprise one or more optical elements in a respective identical optical configuration, which are each arranged next to one another in the same position along a first optical axis of the first lens system channel or a second optical axis of the second lens system channel, wherein the first lens system channel comprises at least one first optical element and the second lens system channel comprises at least one second optical element adjacent the first optical element, wherein a first optical axis of the first optical element coincides with the first optical axis of the first lens system channel and a second optical axis of the second optical element coincides with the second optical axis of the second lens system channel, wherein the cross-sectional area of the first optical element is inscribed in a first circumferential circle and the cross-sectional area of the second optical element is inscribed in a second circumferential circle, the centers of which each coincide with the first optical axis of the first optical element or the second optical axis of the second optical element, and which determine a maximum radius of the first optical element or the second optical element, the first circumferential circle and the second circumferential circle overlap one another, and circumferential shapes of the first optical element and the second optical element deviate from the first and second circumferential circles circumscribing them in such a way that the first optical element and the second optical element do not contact each other.

Within the context of the present disclosure, the feature that the indentation surface of an optical element is inscribed in a circumferential circle means that it does not project beyond the circumferential circle, but can touch the latter at least partially or in places.

In the case of stereo video endoscopes according to the prior art, the circumscribing circumferential circles correspond to the perimeter of the circular optical elements, that is to say for example the perimeter of the lenses. According to the embodiments, the cross-sectional area of the optical elements deviates at least in sections from these circumferential circles. Compared to the circumferential circles, the perimeter of the optical elements is smaller at least in a section of the perimeter facing the respective other optical element. The optical elements consequently have at least one recess compared to circular optical elements. This makes it possible to arrange the first optical element and the second optical element so close to one another that their circumferential circles overlap. The size of the optical elements is therefore no longer limited by the distance of the optical axes of the two lens system channels.

As a result, the distance between the optical axes of the lens system channels and, thus, the strength of the spatial impression can be adjusted. This distance can be reduced in order to counteract a perception as two separate images.

Furthermore, optical elements having a larger diameter can be used in an endoscope having a predefined outer diameter and predefined distance between the optical axes of the lens system channels. Due to the recesses of the optical elements, these can be pushed closer together. This frees up space between the optical elements and the casing tube of the endoscope, which can be utilized by enlarging the diameter of the optical elements. Overall, this attains a higher image quality than with optical elements according to the prior art, since the larger possible diameter of the optical elements more than makes up for the loss of area due to the recesses.

The cross-sectional area of the first optical element and the cross-sectional area of the second optical element can each have the form of a circular segment, wherein the cross-sectional area of the first optical element comprises the center of the first circumferential circle and the cross-sectional area of the second optical element comprises the center of the second circumferential circle, wherein a first chord delimiting the cross-sectional area of the first optical element and a second chord delimiting the cross-sectional area of the second optical element are each arranged perpendicular to a connecting line between the centres of the circumferential circles.

In the context of the present description, a circular segment is understood to denote a segment of a circle, which is delimited by a circular arc and a chord. A circular sector which is delimited by a circular arc and two radii, that is to say has the form of a slice of cake, is not a circular segment.

The form of a circular segment represents an embodiment of an optical element, which is easy to realize in manufacturing terms. In the case of the first optical element and the second optical element, starting from circular optical elements, a part of the cross-sectional area is separated along a chord. The remaining part is larger than the separated part, that is to say it comprises the center of the circumferential circle, the optical axis. The resulting form roughly corresponds to the letter "D", which is why the latter is referred to in this case as a "D-cut". The two optical elements are aligned in the lens system channels such that the rims of the two optical elements defined by the chords face one another.

The first optical element can be mirror-symmetrical to the second optical element with respect to a center line which is arranged centrally between the center of the circumferential circles, and is perpendicular to a connecting line between the centers of the circumferential circles.

The first optical element in the first lens system channel and the second optical element in the second lens system channel are therefore not only arranged next to one another, according to this embodiment, but are also symmetrical with respect to the center line. The cross-sectional areas of the optical elements consequently have the same form and an alignment mirrored around the center line.

Multiple optical elements can comprise the first lens system channel and optical elements arranged as a mirror image thereto can comprise the second lens system channel. Thanks to the arrangement of all of the optical elements in the lens system channels as mirror-image pairs, the optical properties of the lens system channels are the same in mirror image. Only the optical elements arranged in pairs can have a recess, the circumferential circles of which overlap.

In order to achieve a high image quality of the stereoscopic image, powerful optics can be required, which depict the incident light beams on image sensors with a correspondingly high resolution. This requires optical elements with a correspondingly large diameter. In the case of a stereo video endoscope having an outer diameter of 10 mm, the minimum diameter of the optical elements, when using modern high-resolution image sensors, is approximately 3.4 mm. At the same time, in order to realize a stereoscopic effect, it is essential that the distance between the optical axes of the lens system channels is between 2.5 mm and 3 mm. This cannot be achieved with optical elements which have a completely circular cross-sectional area since, in this case, the cross-sectional areas would overlap. The circumferential circles of the optical elements circumscribing the cross-sectional areas therefore can have a diameter of at least 3.4 mm, and a distance between the centers of the circumferential circles is 2.5 mm to 3 mm.

By means of the optical elements, which for example have a D-cut, both conditions can be met. The loss of light caused by the recess of the optical elements is so small that it does not have any significant effect on the image quality. Consequently, it is possible to use powerful optics and high-resolution image sensors in stereo video endoscopes having an outer diameter of 10 mm as well and, consequently, to attain a high image quality and a stereoscopic image.

The first lens system channel can comprise a first image sensor and a first deflection prism, and the second lens system channel can comprise a second image sensor and a second deflection prism, wherein the first image sensor is arranged above and the second image sensor is arranged below a sectional plane spanned by the first optical axis of the first optical element and the second optical axis of the second optical element and both image sensors are aligned plane parallel to the sectional plane, wherein the first deflection element diverts light beams incident in the first lens system channel in the direction of the first image sensor and the second deflection element diverts light beams incident in the second lens system channel in the direction of the second image sensor.

This allows a space-saving design of the optical system. To this end, the image sensors can be arranged in a space-saving way. Usually the image sensors are arranged such that a normal on the surface of the image sensors points in the direction of the optical axes of the lens system channels. By using deflection elements which are, for example, prisms or mirrors, the image sensors can be arranged above or below and plane parallel to the sectional plane. In this way, the space taken up by the image sensors is reduced.

The image sensors can each comprise a light-sensitive surface and a light-insensitive edge, wherein the image sensors, such as the light-insensitive edges of the image sensors, can overlap in a projection onto the sectional plane.

This ensures that the image sensors used in stereo video endoscopes, such as CCD sensors, have a light-insensitive edge due to the manufacturing process such that if the two image sensors are arranged in the same plane, the edges prevent the image sensors from being pushed together such that the light-sensitive surfaces lie in contact with one another. This would waste usable space. However, since the image sensors do not have to lie in the same plane, they can be arranged such that the light-insensitive edges overlap in a projection onto the sectional plane. The image sensors can also be pushed together even further such that the light-sensitive surfaces partially or completely overlap in the projection. As a result, the optical system has a more space-saving design. This makes it possible to use image sensors having larger light-sensitive surfaces, resulting in an increase in the image quality. In addition, the distance between the optical axes of the lens system channels can be reduced if the size of the image sensors has previously specified the minimum distance of the optical axes. The arrangement of the image sensors makes it possible, for the very first time, to attain a stereoscopic effect with large image sensors since, if the image sensors were arranged in one plane, the distance between the optical axes would be too great.

The image sensors can each be arranged on a support, wherein the supports are thinner in a near region with respect to a casing tube of the optical system than in a distant region with respect to the casing tube. The supports are arranged on the side of the image sensors, which is opposite the light-sensitive side of the image sensors. The region of the supports which lies in closest contact with the casing tube delimits the minimum periphery of the casing tube. A casing tube having a smaller diameter or image sensors having larger supports can be used by making this region thinner. Since image sensors with larger supports also have larger light-sensitive surfaces, the image quality of the optical system can be improved in this way.

Light can enter the optical system through an inlet window, wherein the inlet window comprises an inlet surface and an outlet surface and the inlet surface and the outlet surface have finite radii of curvature which are identical to one another. The area of the inlet window specifies how much light can enter the optical system. It is therefore a prerequisite for a high image quality of the optical system that this area is as large as possible. However, the diameter of the inlet window is delimited by the endoscope diameter. In order to increase the area of the inlet window without increasing the diameter of the inlet window, the inlet surface can have a curvature. To prevent an undesirable lens effect of the inlet window occurring due to the curvature of the inlet surface, the outlet surface has a curvature with an identical radius of curvature. In this way, more powerful optics of the optical system are realized and the field of view is enlarged, without reducing the image quality due to an undesirable lens effect of the inlet window.

In a further embodiment of the optical system, an optical element in the first lens system channel and a similar optical element in the second lens system channel are arranged offset to one another. In this way, different path lengths of the light beams, which occur with a sideways looking stereo video endoscope, can be compensated for on entry into the lens system channels.

Such object can be additionally achieved by a stereo video endoscope comprising an optical system in one of the previously described embodiments. The stereo video endoscope has the same or similar advantages, properties or features as the previously described optical system.

BRIEF DESCRIPTION OF THE DRAWINGS

Further features of the embodiments will become evident from the description, together with the claims and the appended drawings. Embodiments can fulfil individual features or a combination of multiple features.

The embodiments will be described below without limiting the general concept of the invention by means of exemplary embodiments with reference to the drawings, wherein reference is expressly made to the drawings regarding all of the details which are not explained in greater detail in the text, wherein:

FIG. 1 illustrates a schematic longitudinal section through an optical system of a stereo video endoscope.

In the drawings, the same or similar elements and/or parts are, in each case, provided with the same reference numerals such that they are not introduced again in each case.

DETAILED DESCRIPTION

Figure 2A:
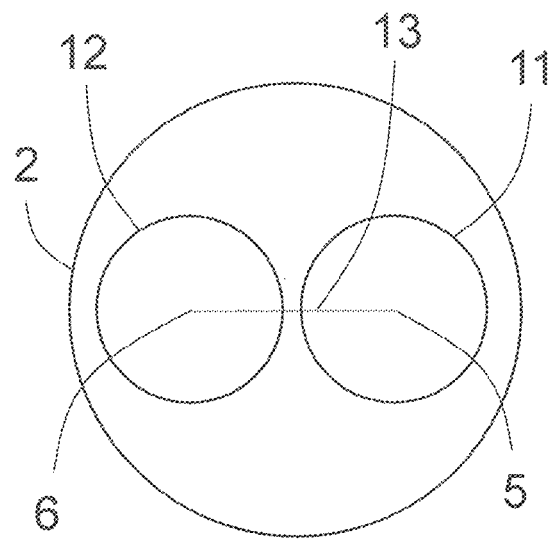
FIG. 2a illustrates a schematic cross-section through an optical system of a stereo video endoscope according to the prior art.

FIG. 1 schematically shows a longitudinal section through an optical system 3 of a sideways looking stereo video endoscope 1. The optical system 3 comprises a first lens system channel 7 with a first optical axis 5 and a second lens system channel 8 with a second optical axis 6. The optical axes 5, 6 are arranged in parallel to one another. At least one first optical element 11 is arranged in the first lens system channel 7 and at least one second optical element 12 is arranged next to the first optical element 11 in the second lens system channel 8. Both lens system channels 7, 8 comprise multiple optical elements, which for better clarity are not all provided with reference numerals in FIG. 1. In addition, the optical system comprises a deflection element 25, 26 and an image sensor 21, 22 in each case for each lens system channel 7, 8.

Light beams, represented in each case by three lines, enter the optical system 3 through an inlet window 30 and an inlet lens 4 and are subsequently guided in the first lens system channel 7 and the second lens system channel 8 in the direction of the deflection elements 25, 26. The first deflection element 25 deflects the light beams in the first lens system channel 7 in the direction away from the drawing plane, while the second deflection element 26 deflects the light beams in the second lens system channel 8 in the direction of the drawing plane. In this way, the light beams are depicted on the image sensors 21, 22 arranged in parallel to the drawing plane, which image sensors convert the light of the incident light beams into image information.

Figure 2B:
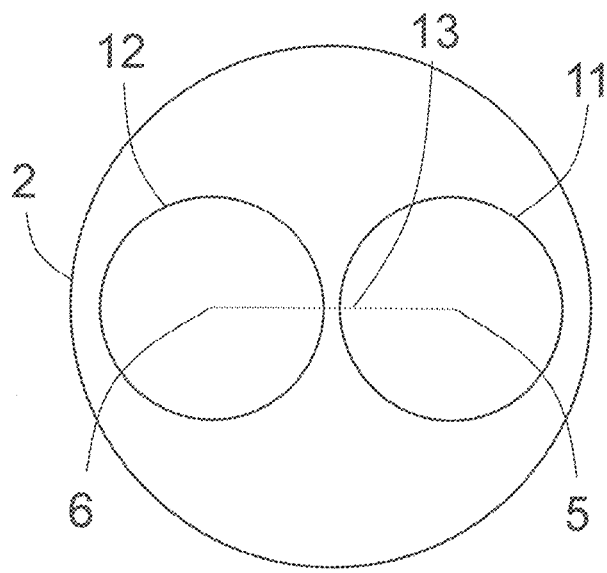
FIG. 2b illustrates a schematic cross-section through an optical system of a stereo video endoscope having an enlarged casing tube diameter.
Figure 2C:
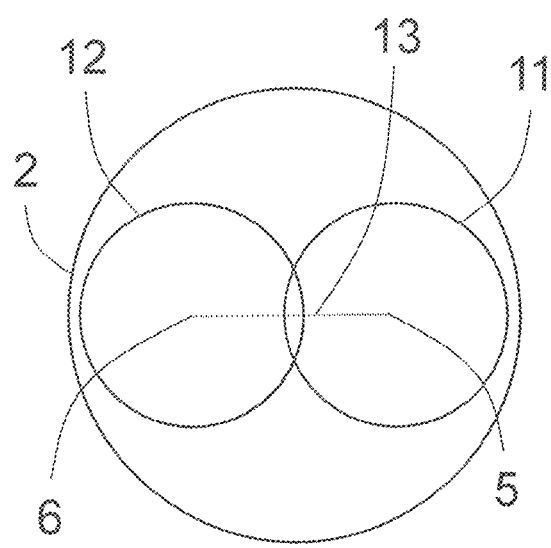
FIG. 2c illustrates a schematic cross-section through an optical system of a stereo video endoscope having overlapping optical elements.
Figure 2D:
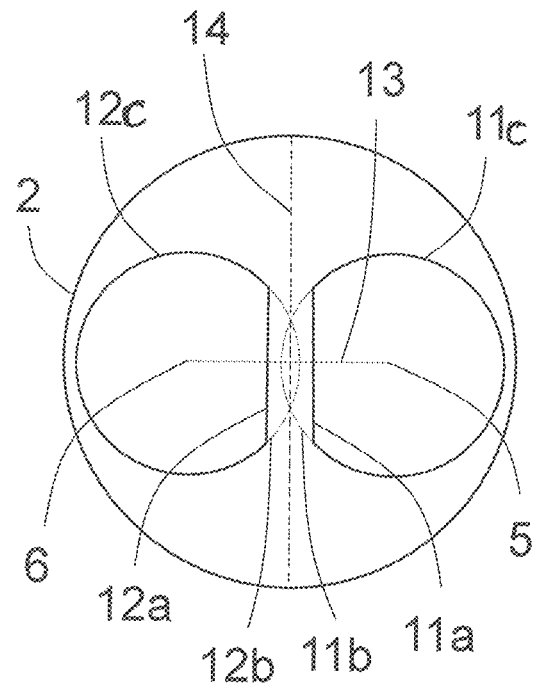
FIG. 2d illustrates a schematic cross-section through an optical system of a stereo video endoscope having optical elements with a D-cut.

FIGS. 2a-2d each show schematic cross-sections through stereo video endoscopes at the level of the optical elements 11, 12. A schematic cross-section through the stereo video endoscope from FIG. 1 along line A-A is shown in FIG. 2d.

FIG. 2a shows a cross-section through the optical system 3 of a stereo video endoscope 1 according to the prior art. The optical elements 11, 12 are lenses which have a circular cross-section. The centers of the lenses, that is to say the optical axes 5, 6 of the optical elements 11, 12 coincide with the optical axes 5, 6 of the lens system channels 7, 8. The distance between the first optical axis 5 and the second optical axis 6, that is to say the length of the connecting line 13, is crucial for the strength of the stereoscopic effect of the stereo video endoscope 1. If the distance is too small, the stereoscopic effect perceived by an observer is weak. If, on the other hand, the distance is too large, the observer perceives two separate images instead of a stereoscopic image. In order to obtain a good stereoscopic image, a suitable distance between the optical axes 5, 6 must therefore be selected. Such a distance is, for example, approximately 2.5 to 3 mm for stereo video endoscopes having an outside diameter of 10 mm. To ensure that the optical elements 11, 12 can be accommodated in the stereo video endoscope 1, the diameter of the optical elements 11, 12 must, in addition, be selected such that these fit into the casing tube 2.

In order to meet these two conditions, optical elements 11, 12 having a comparatively small diameter are usually selected in optical systems 3 according to the prior art. However, in order to obtain a higher image quality, it is necessary to use optical elements 11, 12 having a larger diameter, as shown in FIG. 2b. In order to accommodate the optical elements 11, 12 in the casing tube 2, the diameter of the casing tube 2 has to be enlarged. This results in an enlargement of the diameter of the stereo video endoscope 1, which is undesirable. In addition, the distance of the optical axes 5, 6 is enlarged in FIG. 2b, so that the optical elements 11, 12 can be arranged next to one another. However, in extreme cases, due to the larger distance, a stereoscopic image is no longer perceived by a viewer, but instead two separate images. If, on the other hand, the distance between the optical axes 5, 6 were to be maintained when the optical elements 11, 12 are enlarged, the optical elements 11, 12 would intersect, as shown in FIG. 2c.

In order to solve this problem, the optical elements 11c, 12c can be provided with a so-called D-cut, as shown in FIG. 2d. The cross-sectional areas of the optical elements 11c, 12c have the form of circular segments, wherein the centers of the circumscribing circumferential circles 11b, 12b coincide with the optical axes 5, 6 of the lens system channels. The circular segments are selected to be so large that they include these centers, that is to say the optical axes 5, 6. The circular segments are delimited by chords 11a, 12a. The optical elements 11c, 12c are aligned such that the rims defined by the chords 11a, 12a face one another. The optical elements 11c, 12c are mirror-symmetrical with respect to a center line 14 which runs perpendicular to the optical axes 5, 6 and the connecting line 13 and runs centrally between the optical elements 11c, 12c.

By configuring the optical elements 11c, 12c in the form of a circular segment, the optical axes 5, 6 can be arranged closer to one another than would be the case with optical elements 11, 12 having the same diameter and a completely circular cross-section, as shown in FIG. 2b. In this way, a stereoscopic image is generated even with large optical elements 11c, 12c. In addition, the diameter of the casing tube 2 can also be kept smaller. Compared with the case having smaller optical elements 11, 12 shown in FIG. 2a, more light can be conducted in the direction of the image sensors 21, 22, resulting in a higher image quality.

Such embodiment is not limited to optical elements 11c, 12c which have a D-cut in the form of a chord. The embodiment can likewise comprise optical elements formed in other ways such that the circumferential circles 11b, 12b of the optical elements 11c, 12c overlap. It is thus conceivable, for example, that the rims of the optical elements 11c, 12c are rounded in the region in which the chords 11a, 12a merge with the circular section of the rims of the optical elements 11c, 12c. Even oval shapes are possible according to the embodiment.

Figure 3A:
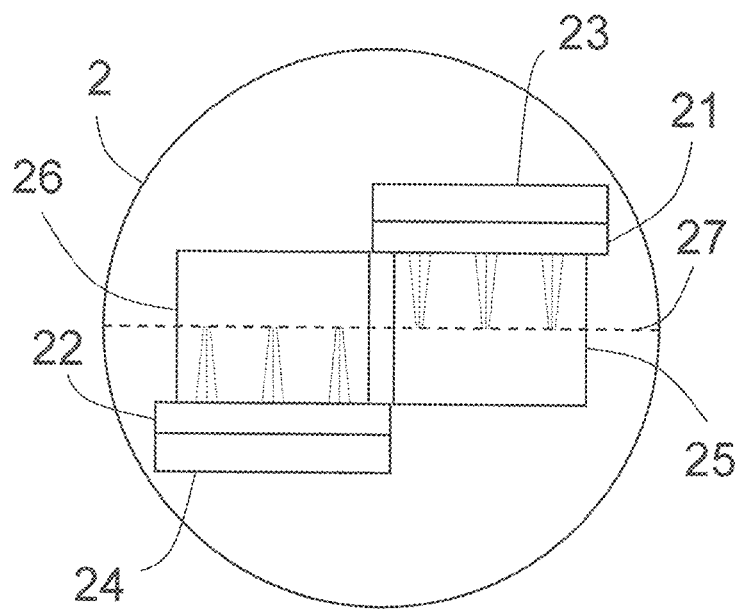
FIG. 3a illustrates a schematic cross-section of an optical system of a stereo video endoscope at the level of the image sensors.

FIG. 3a shows a cross-section through the optical system 3 along the line B-B shown in FIG. 1 with the image sensors 21, 22 which are, for example, CCD sensors. For technical reasons, the image sensors 21, 22 are arranged on supports 23, 24. Both image sensors 21, 22 are aligned in parallel to a sectional plane 27, wherein the first image sensor 21 is arranged above and the second image sensor 22 is arranged below the sectional plane 27. The sectional plane 27 is spanned by the optical axes 5, 6 and the connecting line 13, as shown in FIGS. 2a-2d. Incident light beams, indicated by the dotted lines, are deflected by means of the deflection elements 25, 26, which are for example prisms or mirrors, in the direction of the image sensors 21, 22.

Figure 3B:
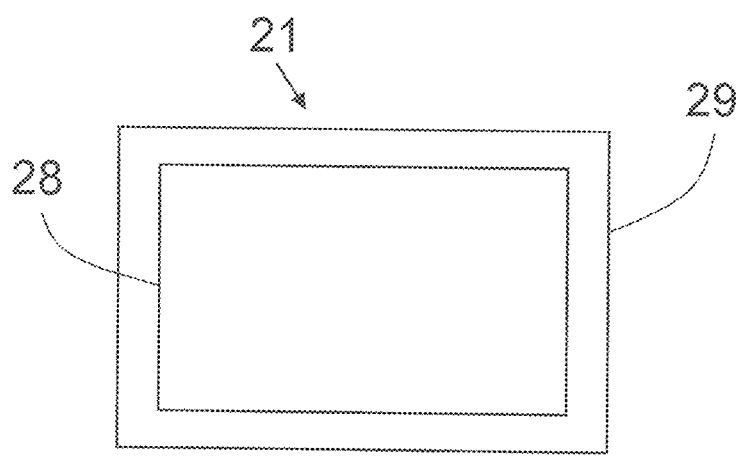
FIG. 3b illustrates a schematic representation of an image sensor.

Thanks to this arrangement of the image sensors 21, 22, the areas of the image sensors 21, 22 can be selected to be so large that they overlap in a projection onto the sectional plane 27. This is crucial since, for technical reasons, the image sensors 21, 22 have a light-sensitive surface 28 and a light-insensitive edge 29, as shown by means of the example of the first image sensor 21 in FIG. 3b. In the case of large image sensors 21, 22, the result is that the image sensors 21, 22 can no longer be arranged so close to one another that the distance of the optical axes 5, 6 required for a stereoscopic perception can be realized. This problem is solved thanks to the arrangement shown in FIG. 3a, since the edges 29 and even the light-sensitive surfaces 28 can overlap in a projection onto the sectional plane 27. The distance of the optical axes 5, 6 can therefore be selected independently of the size of the image sensors 21, 22. In addition, it is possible to use larger image sensors 21, 22 and, consequently, to achieve a higher image quality.

Figure 4:
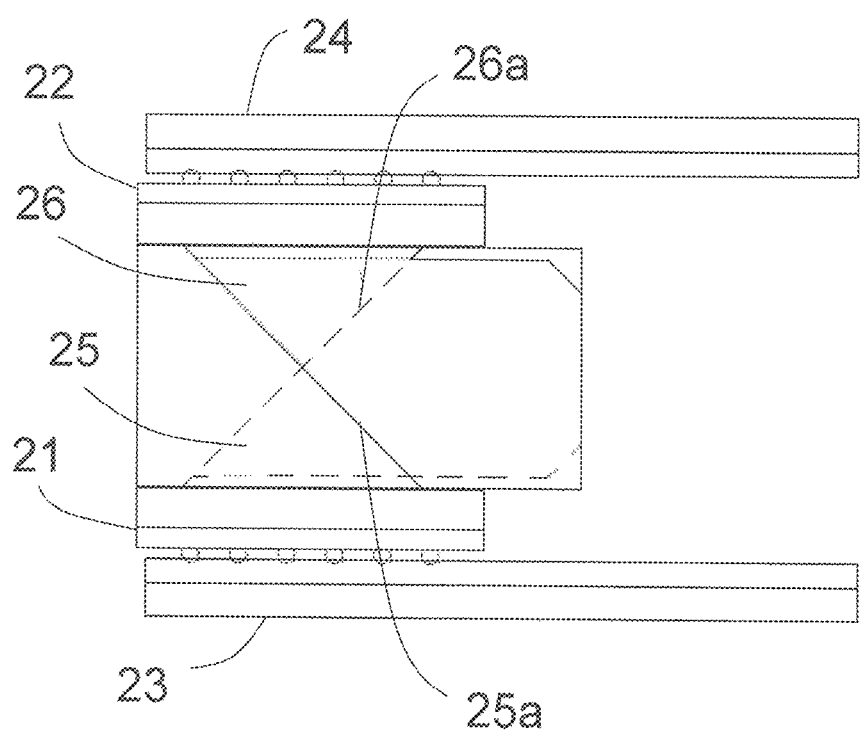
FIG. 4 illustrates a schematic top view of an optical system of a stereo video endoscope at the level of the image sensors.

FIG. 4 schematically shows a top view of the arrangement of the image sensors 21, 22 and the deflection elements 25, 26 shown in FIG. 3a. Consequently, the view corresponds to a view from the direction located at the top in FIG. 1. The reflection surfaces 25a, 26a of the deflection elements 25, 26, which reflect the incident light and deflect it in the direction of the first image sensor 21 or the second image sensor 22, can be seen in this top view.

Figure 5:
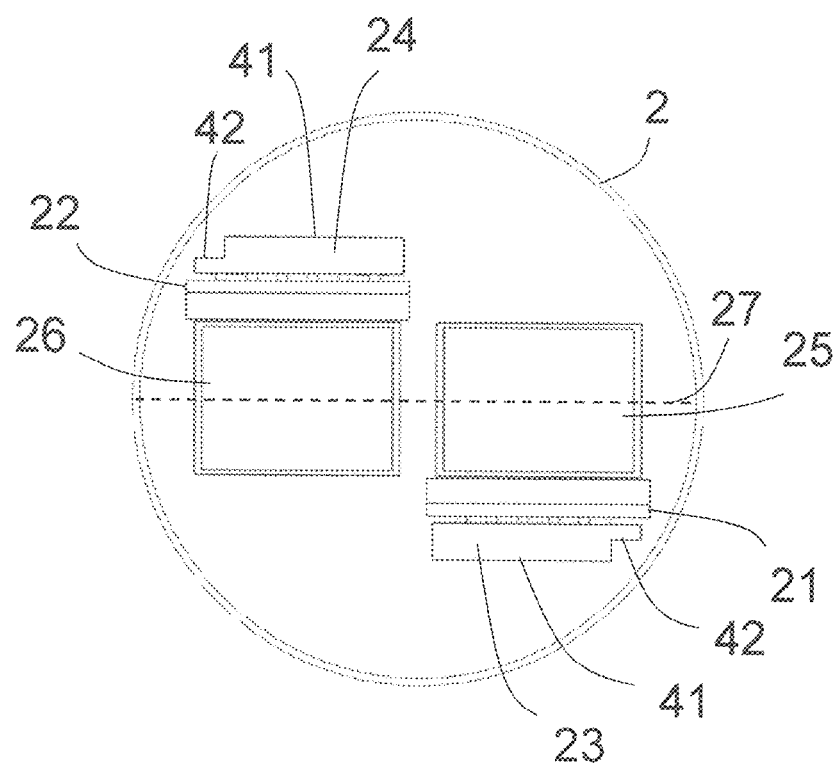
FIG. 5 illustrates a schematic cross-section through an optical system of a stereo video endoscope having image sensors with thinner supports in the region near the casing tube.

A cross-section through the optical system 3, which substantially corresponds to the cross-section shown in FIG. 3a, is shown in FIG. 5, wherein, a mirroring around the sectional plane 27 does however exist. In contrast to FIG. 3a, the supports 23, 24 in FIG. 5 each have a near region 42 and a distant region 41 with respect to the casing tube 2. The thickness of the supports 23, 24 is reduced in the near region 42 compared with the distant region 41. Thanks to the thinner design of the near region 42, the supports 23, 24 have a more space-saving design. This makes it possible, for example, to reduce the diameter of the casing tube 2 or, as shown in FIG. 5, to enlarge the image sensors 21, 22 and the associated supports 23, 24 and thus achieve a higher image quality.

Figure 6A:
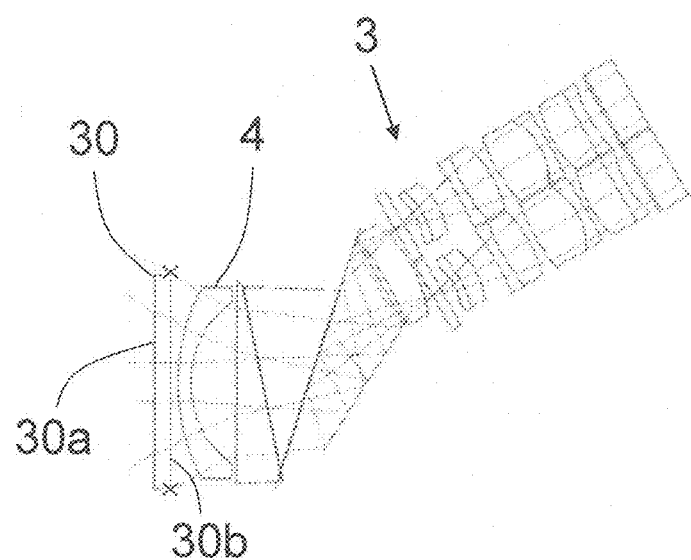
FIG. 6a illustrates a schematic representation of an optical system of a stereo video endoscope according to the prior art.

An optical system 3 of a stereo video endoscope 1 according to the prior art is schematically represented in FIG. 6a. Light beams enter the optical system 3 through a planar inlet surface 30a and a planar outlet surface 30b of the inlet window 30. The size of the inlet window 30 determines how much light enters the optical system 3. The diameter of the inlet window 30 is, however, limited by the diameter of the stereo video endoscope 1. Consequently, the field of view of the endoscope 1 is also limited. This is represented in FIG. 6a in that the outermost light beams represented, which are marked with a "x", cannot enter the optical system 3. For better comparability with the following FIG. 6b, the hypothetical beam path of these light beams in the optical system 3 is nevertheless shown in FIG. 6a.

Figure 6B:
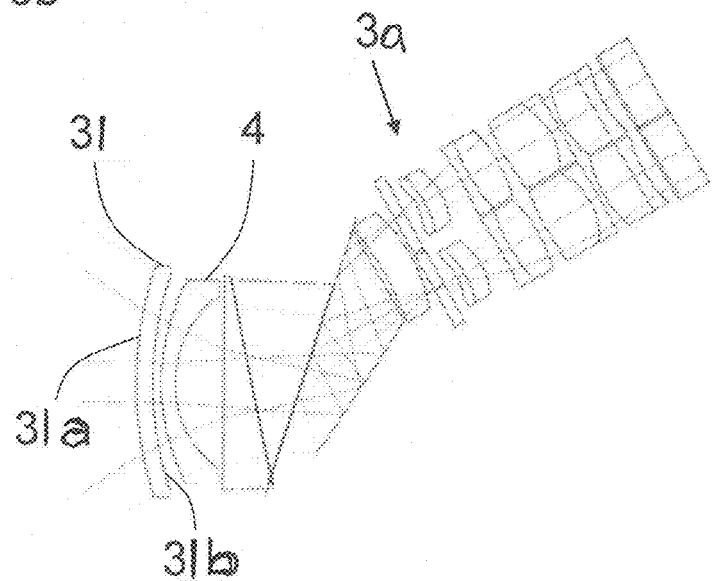
FIG. 6b illustrates a schematic representation of an optical system of a stereo video endoscope having a curved inlet window.

In order to allow more light to enter the optical system 3a and the representable image region to be enlarged, an inlet window 31 is used according to the embodiment shown in FIG. 6b, the inlet surface 31a and outlet surface 31b of which have finite radii of curvature which are identical to one another. This means that the surface of the inlet surface 31a is enlarged while the diameter remains the same. Thanks to the design of the inlet surface 31a as a curved surface, light beams from a larger field of view can enter the optical system 3a, as becomes clear when FIG. 6a is compared with FIG. 6b. In this way, an improvement of the optical properties of the optical system 3a is achieved. The fact that the outlet surface 31b has an identical curvature to the inlet surface 31a prevents the inlet window 31 acting like a lens. A negative effect of the inlet window 31 on the optical properties of the optical system 3a due to an undesirable lens effect is consequently prevented.

Figure 6C:
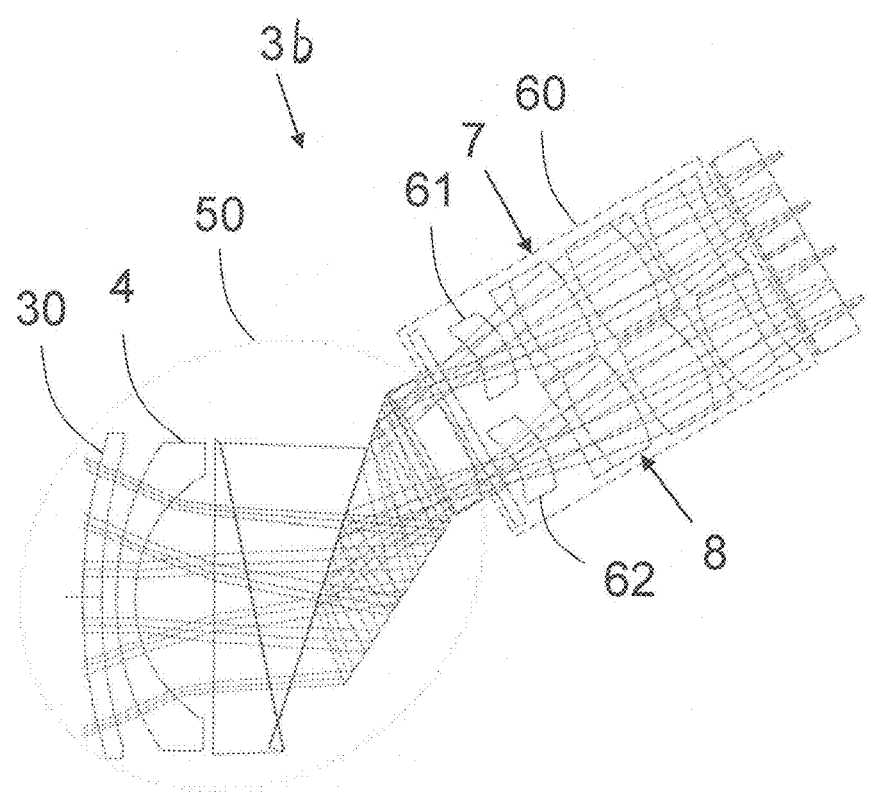
FIG. 6c illustrates a schematic representation of an optical system of a stereo video endoscope having optical elements displaced against one another.

FIG. 6c shows a further embodiment of an optical system 3b. For the sake of better clarity, the distal optical assembly 50 through which light penetrates into the optical system, and the proximal optical assembly 60 which comprises the lens system channels 7, 8, are each identified with dashed lines. In this embodiment, an optical element 61 in the first lens system channel 7 and a, possibly similar, optical element 62 in the second lens system channel 8 are arranged offset to one another. In this way, different beam paths of the light in the distal optical assembly 50 can be compensated such that the image quality of the two images is harmonized and a stereoscopic image with a higher image quality is created.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMERALS

1 Stereo video endoscope
2 Casing tube
3 Optical system
3a Optical System
3b Optical System
4 Inlet lens
5 First optical axis
6 Second optical axis
7 First lens system channel
8 Second lens system channel
11 First optical element
11a First chord
11b First circumferential circle
11c First Optical Element
12 Second optical element
12a Second chord
12b Second circumferential circle
12c Second Optical Element
13 Connecting line
14 Center line
21 First image sensor
22 Second image sensor
23 First support
24 Second support
25 First deflection element
25a First reflection surface
26 Second deflection element
26a Second reflection surface
27 Sectional plane
28 Light-sensitive surface
29 Light-insensitive edge
30 Inlet window
30a Inlet surface
30b Outlet surface
31 Inlet Window
31a Inlet Surface
31b Outlet Surface
41 Distant region
42 Near region
50 Proximal optical assembly
60 Distal optical assembly
61 Optical element
62 Optical element

What is claimed is:

1. An optical system for a stereo video endoscope, the optical system comprising:
a first lens system channel and a second lens system channel for a stereoscopic representation of a region lying outside of the stereo video endoscope,
wherein the first and second lens system channels are arranged in parallel to one another and each comprise one or more optical elements in a respective identical optical configuration, the one or more optical elements of each of the first and second lens system channels being arranged next to one another in a same position along a first optical axis of the first lens system channel and a second optical axis of the second lens system channel, respectively,
the first lens system channel comprises at least one first optical element and the second lens system channel comprises at least one second optical element adjacent to the first optical element,
a third optical axis of the first optical element coincides with the first optical axis of the first lens system channel and a fourth optical axis of the second optical element coincides with the second optical axis of the second lens system channel,
a first cross-sectional area of the first optical element is inscribed in a first circumferential circle and a second cross-sectional area of the second optical element is inscribed in a second circumferential circle, centers of the first and second circumferential circles each coincide with the third optical axis of the first optical element and the fourth optical axis of the second optical element, respectively, to define a maximum radius of the first optical element and the second optical element,
the first circumferential circle and the second circumferential circle overlap one another,
circumferential shapes of the first optical element and the second optical element deviate from the first and second circumferential circles circumscribing them such that the first optical element and the second optical element do not contact each other;
the first lens system channel further comprises a first image sensor and a first deflection element, and the second lens system channel further comprises a second image sensor and a second deflection element,
the first image sensor is arranged on a first side of a sectional plane spanned by the third optical axis of the first optical element and the fourth optical axis of the second optical element, the second image sensor is arranged on a second side of the sectional plane and each of the first and second image sensors are aligned plane parallel to the sectional plane, and the first deflection element diverts light beams incident in the first lens system channel in the direction of the first image sensor and the second deflection element diverts light beams incident in the second lens system channel in the direction of the second image sensor.

2. The optical system according to claim 1, wherein:
the first cross-sectional area of the first optical element and the second cross-sectional area of the second optical element each have the form of a circular segment, wherein the first cross-sectional area of the first optical element comprises a center of the first circumferential circle and the second cross-sectional area of the second optical element comprises a center of the second circumferential circle, and a first chord delimiting the first cross-sectional area of the first optical element and a second chord delimiting the second cross-sectional area of the second optical element are each arranged perpendicular to a connecting line between the centers of the first and second circumferential circles.

3. The optical system according to claim 1, wherein the first optical element is mirror-symmetrical to the second optical element with respect to a center line arranged centrally between the centers of the first and second circumferential circles, and the center line is perpendicular to a connecting line between the centers of the first and second circumferential circles.

4. The optical system according to claim 1, wherein the first and second circumferential circles of the first and second optical elements circumscribing the first and second cross-sectional areas, respectively, have a diameter of at least 3.4 mm, and a distance between the centers of the first and second circumferential circles is 2.5 mm to 3 mm.

5. The optical system according to claim 1, wherein the first and second image sensors overlap in a projection onto the sectional plane.

6. The optical system according to claim 5, wherein the first and second image sensors each comprise a light-sensitive surface and a light-insensitive edge, wherein the light-insensitive edges of the first and second image sensors overlap in the projection onto the sectional plane.

7. The optical system according to claim 1, wherein the first and second image sensors are each arranged on a support, and the supports are thinner in a first region adjacent to a casing tube of the optical system than in a second region further from the casing tube than the first region.

8. The optical system according to claim 1, further comprising an optical inlet window into which light enters the optical system, wherein the inlet window comprises an inlet surface having a first radius of curvature and an outlet surface having a second radius of curvature, where the first radius of curvature is equal to the second radius of curvature.

9. A stereo video endoscope comprising the optical system according to claim 1.

10. An optical system for a stereo video endoscope, the optical system comprising:

a first lens system channel and a second lens system channel for a stereoscopic representation of a region lying outside of the stereo video endoscope, wherein the first and second lens system channels are arranged in parallel to one another and each comprise one or more optical elements in a respective identical optical configuration, the one or more optical elements of each of the first and second lens system channels being arranged next to one another in a same position along a first optical axis of the first lens system channel and a second optical axis of the second lens system channel, respectively, the first lens system channel comprises at least one first optical element and the second lens system channel comprises at least one second optical element adjacent to the first optical element, a third optical axis of the first optical element coincides with the first optical axis of the first lens system channel and a fourth optical axis of the second optical element coincides with the second optical axis of the second lens system channel, a first cross-sectional area of the first optical element is inscribed in a first circumferential circle and a second cross-sectional area of the second optical element is inscribed in a second circumferential circle, centers of the first and second circumferential circles each coincide with the third optical axis of the first optical element and the fourth optical axis of the second optical element, respectively, to define a maximum radius of the first optical element and the second optical element, the first circumferential circle and the second circumferential circle overlap one another, circumferential shapes of the first optical element and the second optical element deviate from the first and second circumferential circles circumscribing them such that the first optical element and the second optical element do not contact each other; and wherein the first and second circumferential circles of the first and second optical elements circumscribing the first and second cross-sectional areas, respectively, have a diameter of at least 3.4 mm, and a distance between the centers of the first and second circumferential circles is 2.5 mm to 3 mm.

* * * * *